United States Patent [19]

Brown et al.

[11] Patent Number: 4,581,012

[45] Date of Patent: Apr. 8, 1986

[54] MULTILUMEN CATHETER SET

[75] Inventors: Eric W. Brown, Redondo Beach; Henry T. Tai, Pacific Palisades, both of Calif.; Robert M. Asher, Quincy, Mass.

[73] Assignee: I-Flow Corporation, Redondo Beach, Calif.

[21] Appl. No.: 678,481

[22] Filed: Dec. 5, 1984

[51] Int. Cl.[4] ............................................. A61M 25/00
[52] U.S. Cl. ..................................... 604/43; 604/175; 604/283
[58] Field of Search ....................................... 604/43–45, 604/175, 283; 285/137 R

[56] References Cited

U.S. PATENT DOCUMENTS

| | | | |
|---|---|---|---|
| 243,396 | 6/1881 | Pfarre . | |
| 550,238 | 11/1895 | Allen, Jr. . | |
| 1,696,018 | 12/1928 | Schellberg . | |
| 2,173,527 | 9/1939 | Agayoff | 128/349 |
| 2,845,930 | 8/1958 | Brown | 128/348 |
| 2,854,982 | 10/1958 | Pagano | 128/348 |
| 2,936,761 | 5/1960 | Snyder | 128/349 |
| 2,976,865 | 3/1961 | Shipley | 128/2.05 |
| 3,046,988 | 7/1962 | Moreau et al. | 128/325 |
| 3,055,361 | 9/1962 | Ballard | 128/214 |
| 3,144,868 | 8/1964 | Jascalevich | 128/350 |
| 3,359,974 | 12/1967 | Khalil | 128/2.05 |
| 3,370,587 | 2/1968 | Vizcarra | 128/214.4 |
| 3,435,819 | 1/1969 | Reynolds et al. | 128/2.05 |
| 3,437,088 | 4/1969 | Bielinski | 128/2 |
| 3,566,874 | 3/1971 | Shepard | 128/349 |
| 3,583,404 | 6/1971 | McWorter | 128/349 |
| 3,640,269 | 2/1972 | Delgado | 128/2 R |
| 3,695,921 | 10/1972 | Shepard et al. | 117/72 |
| 3,726,281 | 4/1973 | Norton et al. | 128/349 |
| 3,815,608 | 6/1974 | Spimosa et al. | 128/349 |
| 3,867,945 | 2/1975 | Long | 128/349 |
| 3,885,567 | 5/1975 | Ross | 128/278 |
| 3,885,820 | 5/1975 | Trumbell et al. | 285/137 R |
| 3,995,623 | 12/1976 | Blake et al. | 128/2.06 |
| 4,057,065 | 11/1977 | Thow | 128/348 |
| 4,072,146 | 2/1978 | Howes | 128/2.05 |
| 4,100,246 | 7/1978 | Frisch | 264/230 |
| 4,106,509 | 8/1978 | McWhorter | 128/349 |
| 4,150,673 | 4/1979 | Watt | 285/137 R X |
| 4,228,802 | 10/1980 | Trott | 128/349 |
| 4,300,550 | 11/1981 | Gandi et al. | 128/207 |

(List continued on next page.)

FOREIGN PATENT DOCUMENTS 960932  1/1975  Canada ............................... 128/127

OTHER PUBLICATIONS

Advertisement for Howe's Multi-Infusion Catheter System Sanders, "Experience with Double Lumen Right Atrial Catheters", *Journal of Parenteral and Eteral Nutrition*.
Gray et al., "Multiple Use of TPN Catheter is Not Heresy: Retrospective Study," *Nutritional Support Services*.
Anderson et al., "The Double-Lumen Hickman Catheter", American Journal of Nursing.
Advertisement for a Multi-Med Infusion Catheter.
The Swanz-Ganz Flow-Directed Monitoring Catheters.
*Standard Wall Catheters* Including the Cournand Double Lumen and the Fox-Fry Catheter.
Cournand et al., "Double Lumen Catheter for Intravenous and Intracardiac Blood Sampling and Pressure Recording".

*Primary Examiner*—Dalton L. Truluck
*Attorney, Agent, or Firm*—Robert M. Asher

[57] ABSTRACT

A subcutaneously tunneled catheter set is disclosed in which a first multilumen catheter is connected to a second reinforced multilumen catheter. A tissue cuff is located near the connection between the two catheter tubes. The disclosure includes a multilumen connector made from a housing that provides conduits between two sets of ports which connect to catheter tubes at either end. The tissue cuff is connected around the outside of the multilumen connector. A multilumen locking connector is provided so that the subcutaneously tunneled multilumen catheter set may be connected directly to an exterior multilumen catheter tube.

13 Claims, 8 Drawing Figures

U.S. PATENT DOCUMENTS

| | | | |
|---|---|---|---|
| 4,318,402 | 3/1982 | Vallancourt | 128/214.4 |
| 4,328,806 | 5/1982 | Cooper | 128/349 |
| 4,329,993 | 5/1982 | Lieber et al. | 128/349 |
| 4,335,719 | 6/1982 | Johnston | 128/246 |
| 4,367,740 | 1/1983 | Evanoski | 604/43 |
| 4,377,169 | 3/1983 | Banks | 604/8 |
| 4,385,631 | 5/1983 | Uthmann | 604/284 |
| 4,402,684 | 9/1983 | Jessup | 604/264 |
| 4,403,984 | 9/1983 | Ash et al. | 604/50 |
| 4,405,313 | 9/1983 | Sisley et al. | 604/43 |
| 4,406,656 | 9/1983 | Hattler et al. | 604/280 |
| 4,407,304 | 10/1983 | Lieber et al. | 128/786 |
| 4,430,076 | 2/1984 | Harris | 604/96 |
| 4,432,853 | 2/1984 | Banks | 204/192 |
| 4,478,436 | 10/1984 | Hashimoto | 285/137 R |

U.S. Patent   Apr. 8, 1986   4,581,012
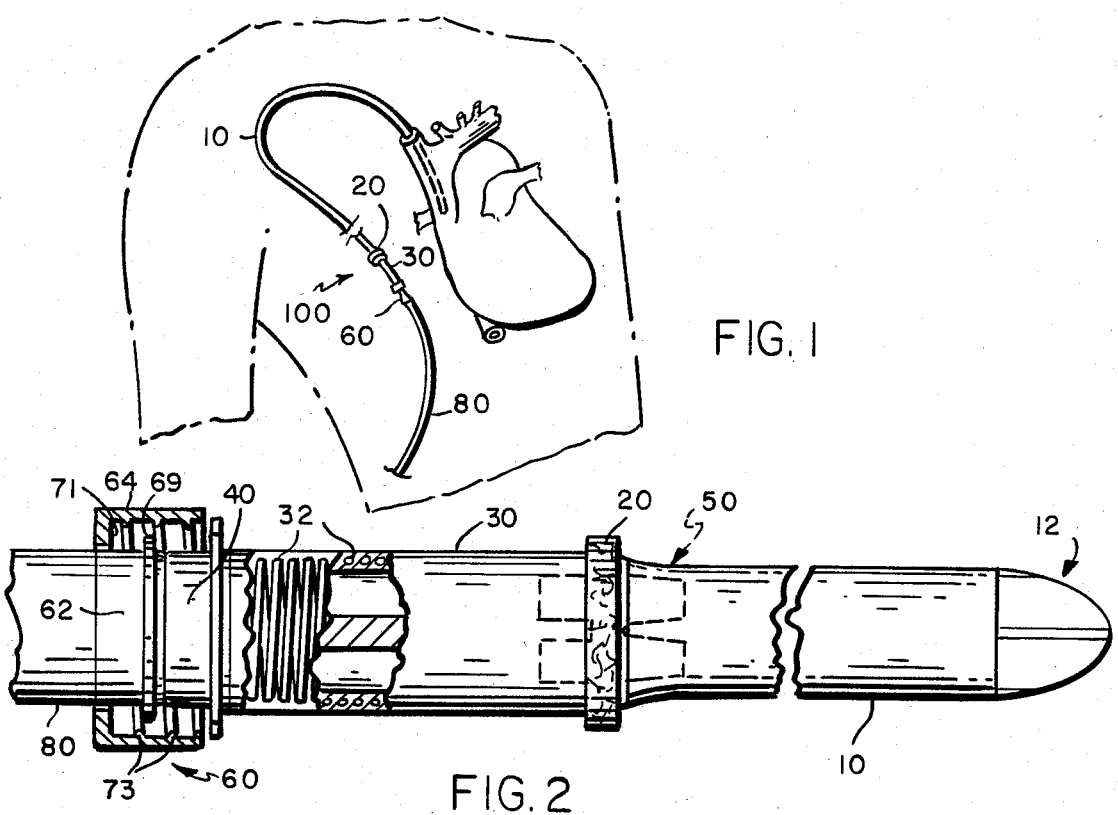
FIG. 1
FIG. 2
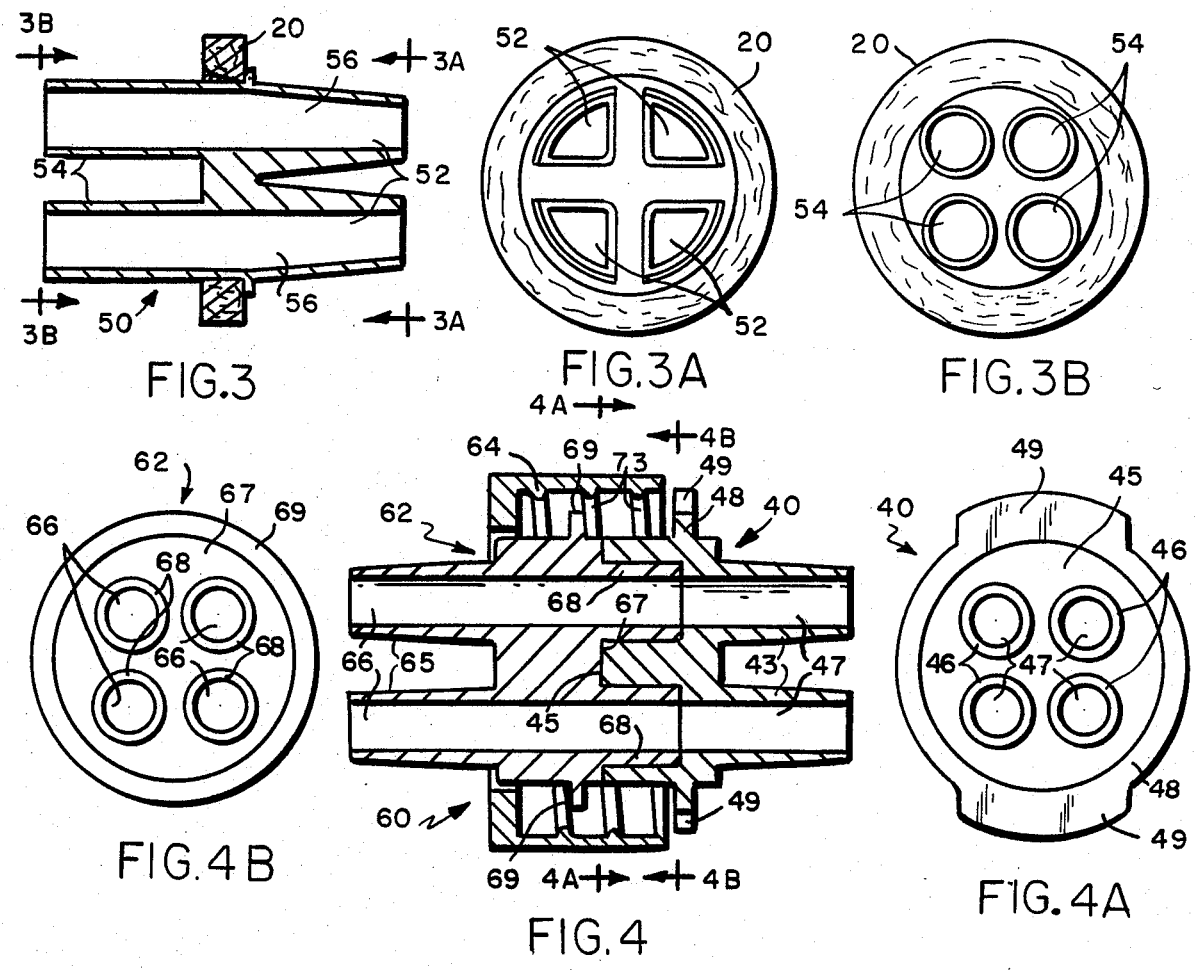
FIG. 3
FIG. 3A
FIG. 3B
FIG. 4B
FIG. 4
FIG. 4A

MULTILUMEN CATHETER SET

BACKGROUND OF THE INVENTION

This invention relates to a multilumen catheter set, in particular, one for a subcutaneous route for intravenous infusions.

It has been found convenient for patients who are receiving frequent infusions to provide them with a tunneled subcutaneous catheter. Such a catheter is inserted underneath the skin of the patient and then into a vein. A tissue cuff is provided on the catheter near the skin so that the skin may grow into it and hold the catheter in place. An adapter is located on the end of the catheter, above the skin, into which a mating connector may be attached to connect the subcutaneously tunneled catheter with an external catheter. The external catheter may be used for infusion of fluids or for extraction of body fluid for testing.

Since there are times when more than one infusion or operation using the catheter set may be desirable, dual lumen subcutaneously tunneled catheters have been developed. The two lumens are fused together underneath the skin of the patient. Above the skin the lumens are separated and each is provided with an adapter for separate connection to an outside source.

Experimentation and advances in medicine are creating new needs for infusing a multiplicity of fluids into a patient. There are many applications for which there is a need for a device which can intravenously administer a plurality of drug solutions. One such application is the use of chemotherapy to treat such diseases as cancer. Attempts at providing more advanced chemotherapy regimens involving the intravenous administration of a multiplicity of drug solutions are being inhibited by a lack of equipment to simplify such a procedure. Very often if different drug solutions are used, they are administered by using a separate catheter tube for each drug. This may require a separate pump for each catheter tube line which would increase costs. There is thus a need for new catheter equipment which can allow doctors to more easily experiment and use new treatments involving a plurality of drug solutions.

SUMMARY OF THE INVENTION

The present invention is directed to a subcutaneously tunneled catheter set which includes a first multilumen catheter for insertion under the skin of a patient. A second reinforced multilumen catheter is provided to prevent kinking of the catheter tube hanging from the patient. A connector is provided to connect the lumens of the reinforced catheter to the lumens of the subcutaneously tunneled catheter. A tissue cuff is located near the connection between the two catheters. According to the preferred embodiment, the connector between the subcutaneous catheter and the reinforced catheter includes a tissue cuff about its circumference.

At the outermost end of the reinforced catheter a multilumen locking connector is attached. The connector includes a first lock adapter which is attached to the reinforced catheter. The adapter includes a plurality of ports for connection with each of the lumens in the reinforced catheter. A conduit is located in the adaptor between each port and a mating face. A second lock adapter is attached to an external catheter for connection to the subcutaneously tunneled catheter set. The second lock adapter includes a plurality of ports and conduits connecting its ports to a second mating face. A device is provided for locking the two adapters together. They are locked in such a way that the mating faces abut one another and the conduits provide communication between the lumens of the external catheter and the lumens of the reinforced subcutaneously tunneled catheter.

The multilumen catheter set of the present invention advantageously provides the ability for long term regimens of drug treatment involving a plurality of drug solutions. The wire reinforced catheter advantageously avoids blockage of the catheter because of bending of the catheter tube. The multilumen locking connector allows the use of an external multilumen catheter with the subcutaneously tunneled catheter set, thereby eliminating any need for a plurality of separate catheters which may require separate pumps and would be more cumbersome and likely to become entangled.

A single pump which may be used in conjunction with the catheter set of the present invention is described in copending patent application entitled "Infusion Pump", sharing the same assignee and filing date as the present invention. The disclosure of said application being hereby incorporated by reference herein.

Other objects and advantages of the present invention will become apparent during the following description of the presently preferred embodiment of the invention taken in conjunction with the drawings.

BRIEF DESCRIPTION OF THE DRAWINGS

FIG. 1 is an illustration of the catheter set of the present invention being used in a patient.

FIG. 2 is a plan view of the catheter set of the present invention in partial cross-section.

FIG. 3 is a cross-sectional view of the multilumen connector of the present invention.

FIG. 3A is an end view of the multilumen connector of FIG. 3 taken along lines A—A.

FIG. 3B is an end view of the multilumen connector of FIG. 3 taken along lines B—B.

FIG. 4 is a cross-sectional view of the multilumen locking connector of the present invention.

FIG. 4A is an end view of the multilumen locking connector of FIG. 4 taken through lines A—A.

FIG. 4B is an end view of the multilumen locking connector of FIG. 4 taken through lines B—B.

DETAILED DESCRIPTION OF THE PREFERRED EMBODIMENT

Referring now to FIG. 1, the multilumen subcutaneously tunneled catheter set 100 of the present invention is inserted and used in a patient in a manner similar to that of the well known Hickman catheter sets. According to the present invention, a subcutaneously tunneled multilumen catheter tube 10 is surgically inserted under the skin and into a vein of the patient. The lumens are provided with an exit port 12 at the end of the multilumen catheter tube 10. At the other end of the subcutaneously tunneled multilumen catheter tube there is a tissue cuff 20 into which fibrous tissue of the patient grows to anchor the catheter set and to reduce the likelihood of infection.

A reinforced catheter tube 30 extends from the tissue cuff 20 out of the patient and ends with a multilumen locking connector adapter 40. Since the catheter tubes are very small in diameter bending a multilumen catheter tube may have a tendency to close off one of the lumens with a kink in the outer layer of tubing. To make the exterior catheter tube kink-proof, reinforcement is provided in the multilumen catheter 30. In accordance with the preferred embodiment as shown in FIG. 2, the catheter 30 is reinforced with a wire coil 32. The wire coil 32 may be additionally used in some applications to conduct electrical information from a sensor located at the patient's body back to diagnostic instruments. The multilumen locking connector adaptor 40 is covered by a heparin cap when the catheter set is not in use. In a multilumen catheter, since the walls of each lumen are often much smaller than the walls of a single catheter tube, the likelihood of a blockage due to kinking when the tube is bent is greater. To make the exterior catheter tube kink-proof, reinforcement is provided in the multilumen catheter 30. In accordance with the preferred embodiment as shown in FIG. 2, the catheter 30 is reinforced with a wire coil 32. The wire coil 32 may be additionally used in some applications to conduct electrical information from a sensor located at the patient's body back to diagnostic instruments.

Referring now to FIGS. 3, 3A and 3B, the multilumen connector of the present invention is shown. This connector 50 has a plurality of ports 52 at one end onto which the lumens of the subcutaneously tunneled multilumen catheter tube 10 are bonded in a conventional manner. At the opposite end of the connector 50, a corresponding plurality of ports 54 are provided for bonding with the lumens of the reinforced catheter 30. The shapes of the lumens illustrated in FIGS. 3A and 3B differ. Nevertheless, the lumens in the multilumen catheters of the present invention may be any useable shape and they may be the same at both ends of the connector 50. It is desirable however that the lumens be shaped in the subcutaneously tunneled multilumen catheter tube so that the maximum amount of fluid flow is allowed in a minimum amount of space. The ports 52 and 54 at opposite ends of the connectors are in communication with one another via conduits 56. Thus when the connector is hooked up on either end to a multilumen catheter tube, the lumens of the two tubes are in communication with one another. According to the present invention, the preferred placement for the tissue cuff 20 is around the outer circumference of the multilumen connector 50 as shown in FIG. 3. The cuff 20 may be glued, thermally melted or bonded to the connector 50 by any other conventional bonding method.

FIGS. 4, 4A and 4B illustrate the multilumen locking connector for connecting the catheter set of the present invention with an external multilumen catheter tube 80. The external multilumen catheter tube 80 is preferably reinforced to avoid kinking. According to the preferred embodiment the multilumen locking connector 60 is made with a female locking adapter 40, a male locking adapter 62 and a locking ring 64. The female locking adapter 40 includes a plurality of ports 43 onto which the lumens of the reinforced catheter tube 30 are bonded. On the opposite side of the female lock adapter 40 is a mating face 45 which includes a plurality of indentations 46. A conduit 47 passes from each port 43 to the mating face 45. The indentations 46 are located at each conduit 47. A ring 48 including two tabs 49 is shown surrounding the outer circumference of the female adapter 40. The tabs 49 are used for engaging the locking ring 64.

The male multilumen locking adapter 62 is likewise provided with a plurality of ports 65 for fitting within and bonding to its respective multilumen catheter tube. Conduits 66 connect each port 65 to the mating face 67 at the other end of the male adapter 62. The mating face 67 of the male locking connector includes a protrusion 68 at each conduit 66. The protrusions 68 match the indentations 46 of the female locking connector 40 so that the two mating faces 67 and 45 may be interengaged.

The lumens in a multilumen catheter are symmetrically arranged about the center. The conduits in the multilumen locking connector 60 may likewise be symmetrically arranged. However, it may be useful to provide asymmetry or a matching groove and notch in the two mating faces so that the mating facings cannot be interengaged in any other than one position. This will ensure that each time an exterior multilumen catheter tube 80 is attached to the subcutaneously tunneled multilumen catheter set 100 the same lumens will be connected. Therefore, the same drug solutions may be delivered through the plurality of lumens without fear of unwanted mixing in the subcutaneously tunneled catheter set 100. The asymmetry about the center may be provided by giving an irregular shape to one or more of the protrusions and indentations or by an asymmetric positioning of the protrusions and indentations which may be accommodated by directing the conduits in other than a straight line.

The male locking connector 62 is provided with a shoulder 69 on its outer circumference. The shoulder 69 is provided for abutment against the locking ring 64. The locking ring 64 includes a base 71 and a set of inner threads 73. The base 71 encircles the male locking adapter 62 and is located at the side of the shoulder 69 near the ports 65. Upon interengagement of the faces of the male and female locking adapters, the locking ring 64 may be screwed onto the female locking adapter 40. The tabs 49 of the female locking adapter 40 engage the threads 73 of the locking ring 64 as it is being screwed. When the base 71 of the ring 64 comes into abutment with the shoulder 69 of the male locking adapter 62, the locking ring 64 will be pulling the male and female locking adapters together and may thereby provide a tight seal.

According to the present invention, it is no longer necessary to provide a number of single lumen catheters for infusing a patient with a plurality of drug solutions. The present invention advantageously provides the ability to hook a single multilumen catheter to the patient for provision of an infusion regimen involving a number of drug solutions. This is especially advantageous where the drug solutions may not be mixed together and provided in a single tube.

Of course, it should be understood that various changes and modifications to the preferred embodiment described above will be apparent to those skilled in the art. For example, a snapping mechanism may be used to replace the screwing ring of the multilumen locking connector. This and other changes can be made without departing from the spirit and scope of the invention and without diminishing its attendant advantages. It is therefore intended that such changes and modifications be covered by the following claims.

We claim:

1. A subcutaneously tunneled catheter set comprising:
    a first multilumen catheter having an exit port for each lumen at one end, said catheter being used for insertion into a patient;

a second multilumen catheter including reinforcement means for preventing the lumens from kinking closed;

a housing for connecting the lumens of said first multilumen catheter with the lumens of said second multilumen catheter, said housing having multiple ports on one side connected by conduits to multiple ports on an opposite side; and a tissue cuff connected around the outside of said housing.

2. The subcutaneously tunneled catheter set of claim 1 wherein said reinforcement means comprises a wire coil.

3. A subcutaneously tunneled catheter set comprising:

a first multilumen catheter having an exit port for each lumen at one end, said catheter being used for insertion into a patient;

a second multilumen catheter including reinforcement means for preventing the lumens from closing when said catheter is bent;

means for connecting the lumens of said first multilumen catheter with the lumens of said second multilumen catheter;

a tissue cuff located near the connection between said first and second catheters for anchoring the catheter set to the patient's skin;

said second multilumen catheter being connected to said connecting means at one end and to a lock adapter at the other end, said lock adapter including a plurality of ports that fit into the lumens of said second catheter and a plurality of conduits each connected to a different one of said ports; and said lock adapter being connectable with a second lock adapter to provide communication between said subcutaneously tunneled catheter set and a third multilumen catheter.

4. The subcutaneously tunneled catheter set of claim 3 wherein said reinforcement means comprises a wire coil.

5. The subcutaneously tunneled catheter set of claim 3 wherein said connecting means comprises a housing having a plurality of conduits connecting a plurality of ports at one end of said housing with a plurality of ports at an other end of said housing, said ports being arranged and shaped at each end to allow a multilumen catheter to fit onto said ports.

6. The subcutaneously tunneled catheter set of claim 5 wherein said tissue cuff is connected around the outside of said connecting means.

7. A multilumen connector comprising:

a housing having a plurality of conduits connecting a plurality of ports at one end of said housing with a plurality of ports at an other end of said housing, said ports being arranged and shaped at each end to allow a multilumen catheter to fit onto said ports; and a tissue cuff attached around the outside of said housing.

8. A multilumen locking connector comprising:

a first lock adapter including a plurality of ports for connection with a first multilumen catheter, a first mating face and a conduit for each port connecting said port to said first mating face;

a second lock adapter including a plurality of ports for connection with a second multilumen catheter, a second mating face and a conduit for each port connecting said port to said second mating face; and means for locking said first lock adapter to said second lock adapter;

said first mating face being interengageable with said second mating face so that the conduits of said first lock adapter interconnect with the conduits of said second lock adapter.

9. The multilumen locking connector of claim 8 wherein said locking means comprises:

thread engageable means extending from said first lock adapter;

shoulder means extending from said second lock adapter; and an internally threaded lock ring having a base for abutting said shoulder means so that when said ring is screwed onto the thread engaging means of said first lock adapter, the first mating face is pulled into sealing contact with the second mating face.

10. The multilumen locking connector of claim 8 further comprising means for preventing the mating faces from being interengaged in any other than one position.

11. The multilumen locking connector of claim 8 wherein one of said mating faces protrudes at each intersection of the conduits with said mating face and the other of said mating faces is indented where the conduits meet the mating face such that the protrusions of said one mating face fit within the indentations of the other mating face.

12. The multilumen locking connector of claim 11 wherein said indentations and said protrusions are asymmetrically arranged or shaped so that there is only one position in which the mating faces can be interengaged.

13. A subcutaneously tunneled catheter set comprising:

a first multilumen catheter having an exit port for each lumen at one end, said catheter being used for insertion into a patient;

a second multilumen catheter including reinforcement means for preventing the lumens from kinking closed;

means for connecting the lumens of said first multilumen catheter with the lumens of said second multilumen catheter, and a tissue cuff connected around the outside of said connecting means.

* * * * *